United States Patent [19]

Kukes et al.

[11] Patent Number: 4,568,788
[45] Date of Patent: Feb. 4, 1986

[54] OLEFIN DISPROPORTIONATION AND CATALYST THEREFOR

[75] Inventors: Semyon Kukes; Robert L. Banks, both of Bartlesville, Okla.

[73] Assignee: Phillips Petroleum Company, Bartlesville, Okla.

[21] Appl. No.: 207,565

[22] Filed: Nov. 17, 1980

[51] Int. Cl.$^4$ .............................................. C07C 6/00
[52] U.S. Cl. .................................. 585/646; 502/240; 502/242; 502/250; 585/644; 585/645
[58] Field of Search ...................... 585/645, 646, 644

[56] References Cited

U.S. PATENT DOCUMENTS 3,579,602  5/1971  Rensser ......................... 585/644 X
3,637,891  1/1972  McGarth et al. ............... 585/644 X
3,865,751  2/1975  Banks et al. .................... 585/646 X

FOREIGN PATENT DOCUMENTS 1264127  2/1972  United Kingdom ............... 585/645

Primary Examiner—Robert V. Hines

[57] ABSTRACT

An improved olefin disproportionation catalyst produced by contacting an inorganic refractory oxide containing a catalytic amount of molybdenum oxide with a promoting amount of at least one elemental metal selected from the group consisting of barium and magnesium.

6 Claims, No Drawings

OLEFIN DISPROPORTIONATION AND CATALYST THEREFOR

BACKGROUND OF INVENTION

This invention relates to the disproportionation of olefins. In another aspect this invention relates to a disproportionation catalyst. In still another aspect, this invention relates to a novel method for producing a disproportionation reaction.

The disproportionation, or metathesis, of olefins is a reaction in which one or more olefinic compounds are transformed into other olefins of different molecular weights. The disproportionation of an olefin to produce one olefin of a higher molecular weight and one olefin of a lower molecular weight can also be referred to as self-disproportionation. For example, propene can be disproportionated to ethylene and cis- and trans-2-butene. Another type of disproportionation involves the codisproportionation of two different olefins to form still other olefins. An example would be the reaction of one molecule of 2-butene with one molecule of 3-hexene to produce two molecules of 2-pentene.

The term "disproportionation reaction" as used herein is intended to include all variations of disproportionation reactions including:

(1) The disproportionation of an acyclic mono- or polyene having at least three carbon atoms into other mono- or polyenes of both higher and lower number of carbon atoms; for example, the disproportionation of propylene yields ethylene and butenes; the disproportionation of 1,5-hexadiene yields ethylene and 1,5,9-decatriene;

(2) The conversion of an acyclic mono- or polyene having three or more carbon atoms and a different acyclic mono- or polyene having three or more carbon atoms to produce different acyclic olefins; for example, the conversion of propylene and isobutylene yields ethylene and isopentene;

(3) The conversion of ethylene and an internal acyclic mono- or polyene having four or more carbon atoms to produce other olefins having a lower number of carbon atoms than that of the acyclic mono- or polyenes; for example, the conversion of ethylene plus 4-methylpentene-2 yields 3-methylbutene-1 and propylene;

(4) The conversion of ethylene or an acyclic mono- or polyene having three or more carbon atoms with a cyclic mono- or cyclic polyene to produce an acyclic polyene having a higher number of carbon atoms than that of any of the starting materials; for example, the conversion of cyclohexene and 2-butene yields 2,8-decadiene; the conversion of 1,5-cyclooctadiene and ethylene yields 1,5,9-decatriene;

(5) The conversion of one or more cyclic mono- or cyclic polyenes to produce a cyclic polyene having a higher number of carbon atoms than any of the starting materials; for example, the conversion of cyclooctene yields cyclohexadiene;

(6) The conversion of an acyclic polyene having at least 7 carbon atoms and having at least 5 carbon atoms between any two double bonds to produce acyclic and cyclic mono- and polyenes having a lower number of carbon atoms than that of the feed; for example, the conversion of 1,7-octadiene yields cyclohexene and ethylene; or (7) The conversion of one or more acyclic polyenes having at least three carbon atoms between any two double bonds to produce acyclic and cyclic mono- and polyenes generally having both a higher and lower number of carbon atoms than that of the feed material; for example, the conversion of 1,4-pentadiene yields 1,4-cyclohexadiene and ethylene.

Among the catalysts that have been developed for disproportionation are those comprising inorganic refractory oxides containing a catalytic amount of molybdenum oxide. The present invention is based upon the discovery of a way to improve the activity of such a catalyst.

SUMMARY OF INVENTION

In accordance with the present invention, a disproportionation catalyst comprising inorganic refractory oxide containing a catalytic amount of molybdenum oxide is improved by contacting said catalyst with a promoting amount of at least one elemental metal selected from the group consisting of barium and magnesium under conditions suitable for said metal to promote the activity said molybdenum oxide. In a preferred embodiment elemental tin is employed in combination with magnesium.

DESCRIPTION OF PREFERRED EMBODIMENTS

The inorganic refractory oxide comprises solid inorganic oxide support containing a major proportion of alumina or silica. Such materials are commonly known as refractory oxides and include, for example, silica, alumina, magnesia-alumina, silica-alumina, titania-alumina, zirconia-alumina, and alumina-titania-zirconia. Preferred refractory metal oxides are alumina or silica refractory oxides, especially high purity forms such as those containing at least 99 percent of alumina or silica. Generally, the refractory oxide has a surface area of at least 25 m$^2$/g and preferably the surface area is from about 100 m$^2$/g.

Molybdenum oxide can be combined with the refractory oxide support in any conventional manner such as dry mixing, impregnation from a diluent, ion exchange, or the like. The oxides can be added directly or in the form of molybdenum compounds that can be converted to oxides by calcination. The calcination is conducted by heating the impregnated refractory oxide in the presence of a nonreducing gas, such as nitrogen, argon, carbon monoxide, or oxygen-containing gas such as air, under conditions sufficient to convert the molybdenum compound to the oxide. Temperatures in the range of about 350° C. to about 800° C. are generally satisfactory for such calcination.

The proportion of the molybdenum oxide combined with the refractory oxide can be varied, but generally the refractory oxide will contain at least 0.1 percent by weight of molybdenum oxide, with amounts from about 0.2 to 50 percent by weight being preferred, and 1 to 15 percent especially preferred, said weight percent being based upon the combined weights of the refractory oxide and the molybdenum oxide.

The molybdenum oxide catalyst is then combined with a promoting amount of an elemental metal selected from magnesium and barium. The amount of promoting metal employed can vary depending upon the level of activation desired. Generally the elemental metal will be employed in an amount in the range of about 0.5 to about 20, preferably about 2 to about 10 weight percent based on the weight of the molybdenum oxide catalyst prior to the addition of the elemental metal. In the preferred embodiment in which elemental tin is employed in combination with magnesium, the elemental tin is employed in an amount in the range of about 1 to about 10, preferably about 2 to about 5 weight percent based on the weight of the molybdenum oxide catalyst prior to the addition of the elemental metals.

The elemental metal can be combined with the catalyst in any suitable manner. The metal in a powdered form can be admixed with the catalyst or more preferably the metal is applied to the catalyst in a molten or vaporous form. This can be accomplished, for instance, by melting the metal and dropping the molten metal on the catalyst or by passing a stream of inert gas such as nitrogen or argon through the molten metal and then over the catalyst.

It is essential that the combination of the elemental metal and the catalyst be heated to an elevated temperature sufficient to cause the promotion to take place. Generally, this involves heating the catalyst to at least the melting temperature of the elemental metal. The length of time heating the catalyst composite is generally in the range of about 1 minute to about 10 hours, preferably on the order of about 10 minutes to about 30 minutes. It is accordingly currently preferred to apply the metal to a bed of the catalyst and then flow a suitable gas, such as nitrogen, through the bed at the melting temperature of the metal for a length of time sufficient to obtain a substantial distribution of the metal in the catalyst. The resulting catalyst is then immediately suitable for use in the disproportionation reaction. Generally the temperature and time required can be determined by observing the catalyst while it is being heated. Generally, there will be an obvious color change in the catalyst which can be used as an indicator that the catalyst is ready for use.

An oxidizing atmosphere has been found to have an adverse effect upon the promoting effect of the elemental metals. Accordingly, it is desirable to protect the promoted catalyst from oxidizing atmosphere particularly while the catalyst is at temperatures greater than about normal room temperature. This can be done by keeping the promoted catalyst under a nondeleterious atmosphere, such as nitrogen, until use.

The promoted catalyst can be used in disproportionation reactions in a conventional manner. The reaction temperature can vary depending upon the type of refractory oxide employed. Typically, the disproportionation is carried out at a temperature in the range of about 100° to about 600° C., preferably about 200° to about 500° C. Generally, a temperature in the range of about 100° to 300° C. is preferred when an alumina support is employed and a temperature in the range of 200° to 500° C. preferred when a silica support is employed.

The disproportionation reaction can be carried out by contacting the olefins to be disproportionated with the catalyst in the liquid phase or the gas phase, depending on structure and molecular weight of the olefins, temperature and pressure.

The pressure during the disproportionation reaction may vary between wide limits. Pressures between 0.1 and 500 atm. are suitable; preferred pressures are between 1 and 40 atm.

If the reaction is carried out in the liquid phase, solvents or diluents for the reactants may be used. Aliphatic saturated hydrocarbons (e.g. pentane, hexane, cyclohexane, dodecane) and aromatic hydrocarbons such as benzene and toluene are suitable. If the reaction is carried out in the gaseous phase, diluents such as aliphatic hydrocarbons (e.g. methane, ethane, and/or substantially inert gases (e.g., nitrogen, carbon dioxide) may be present. Preferably the disproportionation reaction is effected in the absence of dry significant amounts of deactivating materials such as water and oxygen.

The length of time during which the olefinically unsaturated compounds to be disproportionated are contacted with the catalyst is not very critical, and may conveniently vary between 0.1 seconds and 24 hours, although longer and shorter contact times may be used. The contact time needed to obtain a reasonable yield of disproportionated products depends on several factors such as the activity of the catalyst, temperature, pressure and structure of the olefinically unsaturated compounds to be disproportionated.

The process of the invention can be effected batchwise or continuously, with fixed catalyst beds, slurried catalysts, fluidized beds or by using any other conventional contacting techniques. The solid disproportionation catalysts are applied in any appropriate form, for example, as powders, flakes, pellets, spheres or extrudates.

The Products

According to the process of the invention two olefinic reactants are disproportionated to a product comprising olefin(s) having a total number of carbon atoms equal to the sum of the carbon atoms of the two olefinic reactants and having a number of ethylenic linkages equal to the sum of the ethylenic double bonds of the reactants.

One variation of the process comprises the disproportionation of two molecules of the same olefinic reactant. The reaction of two molecules of an acyclic olefin of Formula I generally produces one olefin of a higher carbon number and one olefin of a lower carbon number as depicted in equation (1)

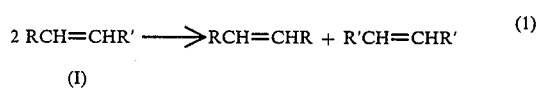

(I)

wherein R and R' have the previously stated significance. If R and R' represent identical groups, it is appreciated that the disproportionation reaction will not cause any skeletal changes as the products RCH=CHR and R'CH=CHR' will be equivalent to R'CH=CHR. By way of specific illustration, the reaction of two molecules of propylene produces ethylene and 2-butene. However, the reaction of two molecules of 2-butene produces two molecules of 2-butene. The reaction of two molecules of cyclic olefinic reactant of Formula II, however, generally produces a cyclic olefin produced as depicted in equation (2)

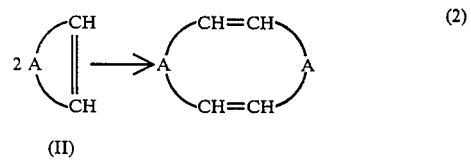

(II)

By way of specific illustration, the reaction of two molecules of cyclooctene produces 1,9-cyclohexadecadiene.

Another variation of the process comprises the disproportionation of two different acyclic olefinic reactants. By way of specific illustration, the reaction of 2-butene and 3-hexene produces two molecules of 2-pentene and the reaction of 2-butene with 1,4-polybutadiene produces two molecules of polybutadiene having a molecular weight which is less than the molecular weight of the starting 1,4-polybutadiene.

Still another variation of the process is "ring-opening" disproportionation wherein an acyclic olefinic reactant represented by Formula I is contacted with a cyclic olefinic reactant represented by Formula II. The product of "ring opening" is a single olefinic compound with one less carbocyclic ring than the cyclic olefinic reactant of Formula II. In terms of the Formulas I and II, the product is represented by Formula III.

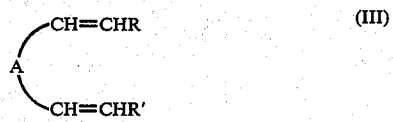

wherein R, R' and A have previously stated significance. By way of specific illustration, from reaction of 2-butene and cyclopentene is produced 2,7-nonadiene. Other typical disproportionation products include 2,8-decadiene produced by reaction of cyclohexene and 2-butene, 3,8-undecadiene produced from 3-hexene and cyclopentene, 1,5,9-decatriene produced by reaction of ethylene and 1,5-cyclooctadiene, and 1,4-divinylcyclohexane from ethylene and bicyclo(2.2.2)oct-2-ene.

In "ring-opening" disproportionation, the cyclic olefinic reactant is preferably a monocyclic or a bicyclic olefinic reactant of up to two ethylenic linkages and most preferably is a monocyclic, monoolefinic reactant of from five to eight carbon atoms, and the acyclic olefinic reactant is preferably an internal olefin which is symmetrical about the double bond, i.e., those olefins wherein both R and R' groups are alkyl and R=R'. The molar ratio of cyclic olefinic reactant to the acyclic olefin in ring-opening disproportionation is not critical, although it is frequently useful to employ a molar excess of the acyclic olefin. Molar ratios of acyclic olefin to cyclic olefin reactant from about 1:1 to about 20:1 are satisfactory with molar ratios from about 1:1 to about 10:1 being preferred.

It is appreciated that an olefinic product produced by any variation of the disproportionation process can undergo further disproportionation with another olefin present in the reaction mixture. For example, 1,6-heptadiene produced from reaction of cyclopentene and ethylene can react with another molecule of cyclopentene to produce 1,6,11-dodecatriene, and 1,9-cyclohexadecadiene produced from reaction of two molecules of cyclooctene can react with additional molecules of cyclooctene to give a high molecular weight monocyclic polyene.

The olefinic products, for the most part, have established utility as precursors of polymers, e.g., as the third component of ethylene-propylene terpolymers useful as synthetic elastomers. Cleavage of the ethylenic bonds of polyolefinic products as by ozonization produces di- or polycarboxylic acids which are reacted with diamines, e.g., hexamethylenediamine, to form Nylons which are useful in synthetic fibers. The olefinic products are converted to secondary and tertiary alcohols as by sulfuric acid-catalyzed hydration. Alternatively, the olefinic products are converted by conventional "Oxo" processes to aldehydes which are hydrogenated with conventional catalysts to the corresponding alcohols. The $C_{12}$–$C_{20}$ alcohols thereby produced are ethoxylated as by reaction with ethylene oxide in the presence of a basic catalyst, e.g., sodium hydroxide, to form conventional detergents and the lower molecular weight alcohols are esterified by reaction with polybasic acids, e.g., phthalic acid, to form plasticizers for polyvinyl chloride.

A further understanding of the present invention and its advantages will be provided by reference to the following examples.

EXAMPLE I

A series of runs were made to determine the effect of temperature on disproportionation of propylene over a silica supported molybdenum oxide catalyst containing about 8 weight percent molybdenum oxide.

In the first run the catalyst was placed in a tubular disproportionation catalyst and calcined at about 550° C. for about 1 hour with flowing air, then flushed with nitrogen and cooled to about 460° C. Then dry substantially pure propylene was passed through the catalyst bed. The reaction temperature was maintained at about 460° C. and samples of the reactor effluent analyzed at given time periods by GLC to determine the percent conversion of propylene. The flow rate of the propylene was about 108 cc/minute.

After this run the catalyst was subjected to calcination in flowing air at 550° C. for about 30 minutes, again flushed with nitrogen and then used for disproportionation of the propylene but this time at 418° C. The flow rate for propylene was about 106 cc/minute.

After this run the catalyst was again subjected to calcination this time at 560° C. for 30 minutes, flushed with nitrogen and then used for disproportionation of the propylene at about 356° C. and a flow rate about 103 cc/minute.

The results of those three runs are summarized in Table I.

TABLE I

| Reaction Temperature | % Propylene Conversion | | | | |
|---|---|---|---|---|---|
| | Time: 15 | 30 | 45 | 60 | 90 |
| 460° C. | 20 | 21 | 21 | 21 | * |
| 418° C. | 15 | 18 | 18 | 18 | 17 |
| 356° C. | 6 | 10 | 11 | 12 | 11 |

*Computer malfunction prevented determination.

These results show that the conversion decreases as the temperature decreases.

EXAMPLE II

In order to evaluate the effect of elemental magnesium, one gram of the 8 percent $MoO_3.SiO_2$ catalyst was placed in the tubular disproportionation reactor and calcined at 550° C. for 40 minutes. The bed was then flushed with nitrogen and 0.03 grams of magnesium added and the temperature increased to about 660° C. to melt the magnesium. That temperature was maintained for about 30 minutes and then the bed cooled to about 350° C. and used to disproportionate the propylene at that temperature and at a flow rate of about 102 cc/minute.

In another run one gram of the 8 percent $MoO_3.SiO_2$ catalyst was placed in the tubular reactor and calcined as in the previous run. The calcined catalyst was purged with nitrogen and a mixture containing 0.03 gram of tin and 0.09 gram of magnesium was added and then the bed heated to melt the metals. In contrast to magnesium alone, the combination of metals melted at about 550° C. Apparently, the combination of metals results in an alloy of lower melting point. The temperature was maintained at about 550° C. for about 30 minutes. Then the bed was cooled to about 353° C. and used in the reaction of propylene. The flow rate was about 104 cc/minute.

In yet another run one gram of the 8 percent $MoO_3$-$SiO_2$ catalyst was placed in the tubular reactor and calcined at about 600° C. for about 30 minutes. The bed was then flushed with nitrogen and 0.05 gram of barium added. The bed was then heated to 730° C. and maintained at that temperature for 30 minutes under flowing nitrogen. It was then cooled and used to disproportionate propylene at about 358°–360° C. The flow rate of propylene was about 103 cc/minute.

The results of these three runs are compared with the closest control run from Example I in the following Table II.

TABLE II

| Catalyst | Reaction Temp, °C. | Time: | 15 | 30 | 45 | 60 | 90 |
|---|---|---|---|---|---|---|---|
| Control | 356° C. | | 6 | 10 | 11 | 12 | 11 |
| 3% Mg | 350° C. | | 22 | 22 | — | 21 | 19 |
| 3% Sn + 9% Mg | 353° C. | | 23 | 25 | 22 | 21 | 20 |

TABLE II-continued

| Catalyst | Reaction Temp, °C. | Time: | 15 | 30 | 45 | 60 | 90 |
|---|---|---|---|---|---|---|---|
| 5% Ba | 358–360° C. | | 12 | 17 | 19 | 17 | 16 |

These results clearly show that elemental magnesium and elemental barium promote the $MoO_3.SiO_2$ catalyst.

What is claimed is:

1. A process for the disproportionation of olefins comprising at least two nonconjugated olefinic reactants under suitable reaction conditions with a catalytic amount of a catalyst composition produced by contacting a refractory oxide containing molybdenum oxide with a promoting amount of a combination of elemental magnesium and elemental tin under conditions suitable for said combination of metals to promote the activity of said molybdenum oxide for the disproportionation reaction.

2. A process according to claim 1 wherein said inorganic refractory oxide is selected from the group consisting of silica, alumina, and mixtures thereof.

3. A process according to claim 2 wherein the molybdenum oxide is combined with the refractory oxide in an amount equal to about 1 to about 15 weight percent of the combined weights of said molybdenum oxide and said refractory oxide.

4. A process according to claim 2 where said refractory oxide comprises silica.

5. A process according to claim 4 wherein each of said elemental magnesium and elemental tin are employed in an amount in the range of about 0.5 to about 20 percent of the combined weights of the molybdenum oxide and the silica prior to the addition of the metals.

6. A process according to claim 5 wherein said olefins comprise propylene.

* * * * *